US008354876B1

(12) United States Patent
Hassibi et al.

(10) Patent No.: US 8,354,876 B1
(45) Date of Patent: Jan. 15, 2013

(54) CHEMICAL DETECTION WITH MOSFET SENSOR

(75) Inventors: Arjang Hassibi, Austin, TX (US); Bahman Hekmatshoartabari, White Plains, NY (US); Ali Khakifirooz, Mountain View, CA (US); Davood Shahrjerdi, White Plains, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 13/550,967

(22) Filed: Jul. 17, 2012

Related U.S. Application Data

(63) Continuation of application No. 13/538,025, filed on Jun. 29, 2012.

(51) Int. Cl.
*H03K 3/01* (2006.01)
(52) U.S. Cl. .......... 327/534; 327/509; 327/530
(58) Field of Classification Search .......... 327/509, 327/530, 534, 545, 546, 548
See application file for complete search history.

(56) References Cited

U.S. PATENT DOCUMENTS

| | | | |
|---|---|---|---|
| 4,437,969 A * | 3/1984 | Covington et al. .......... 257/253 |
| 5,466,348 A | 11/1995 | Holm-Kennedy | |
| 7,317,216 B2 | 1/2008 | Holm-Kennedy | |
| 7,799,205 B2 | 9/2010 | Morgenshtein et al. | |
| 2006/0270053 A1 | 11/2006 | Tilak et al. | |
| 2009/0191649 A1 | 7/2009 | Fukumoto | |
| 2010/0248209 A1 | 9/2010 | Datta et al. | |

OTHER PUBLICATIONS

Chen et al., "Circuit Design Advances for Wireless Sensing Applications", Proceedings of the IEEE, vol. 98, Issue 11, pp. 1808-1827 (Nov. 2010).
Cheng et al., •"Mechanism and Optimization of pH Sensing Using SnO2 Nanobelt Field Effect Transistor", Nano Lett., vol. 8, No. 12, pp. 4179-4184 (2008).
Mescher et al., •"Pulsed Method for Characterizing Aqueous Media Using Nanowire Field Effect Transistors", IEEE Transactions on Electron Devices, vol. 58, No. 7, pp. 1886-1891 (Jul. 2011).
Wipf, "Dual-gated field effect transistors for sensing applications" Master Thesis, University of Basel, pp. 1-51 (Mar. 2010).

* cited by examiner

*Primary Examiner* — Jeffrey Zweizig
(74) *Attorney, Agent, or Firm* — Cantor Colburn LLP; Vazken Alexanian

(57) ABSTRACT

Embodiments relate to a method including receiving a voltage potential at a gate of a first MOSFET based on a sensed chemical characteristic. The method includes receiving at a backgate of the first MOSFET an AC voltage signal and analyzing, with an analysis circuit connected to one of a first source and a first drain of the MOSFET, the sensed characteristic based on the receiving the voltage potential at the gate of the first MOSFET.

20 Claims, 6 Drawing Sheets

US 8,354,876 B1

CHEMICAL DETECTION WITH MOSFET SENSOR

CROSS-REFERENCE TO RELATED APPLICATION

This application is a continuation of U.S. patent application Ser. No. 13/538,025, filed Jun. 29, 2012, the disclosure of which is incorporated by reference herein in its entirety.

BACKGROUND

The present invention relates to metal-oxide-semiconductor field effect transistors (MOSFET) controlled based on sensed chemical characteristics, and more particularly to applying an AC signal to a backgate of a MOSFET to modulate a signal generated based on a sensed chemical characteristic.

Metal-oxide-semiconductor field effect transistors (MOSFET) with chemically sensitive gates or with chemically sensitive electrodes connected to gates are used in gas sensors, ion sensors, bio sensors, etc. However, since chemical signals have a very low frequency, so as to correspond to a substantially direct current (DC) voltage level, measurements are susceptible to MOSFET flicker noise.

SUMMARY

Exemplary embodiments include a method including receiving a voltage potential at a gate of a first MOSFET based on a sensed chemical characteristic, receiving at a backgate of the first MOSFET an AC voltage signal, and analyzing, with an analysis circuit connected to one of a first source and a first drain of the MOSFET, the sensed characteristic based on the receiving the voltage potential at the gate of the first MOSFET.

Additional exemplary embodiments include a method including generating a sensing voltage based on a sensed chemical characteristic, providing the sensing voltage to a gate of a first MOSFET, and modulating the sensing voltage with an AC voltage signal applied to a backgate of the first MOSFET to generate a modulated sensing signal.

Additional features and advantages are realized through the techniques of the present disclosure. Other embodiments and aspects of the present disclosure are described in detail herein and are considered a part of the claimed invention. For a better understanding of the invention with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

In exemplary embodiments, an AC signal is provided to a backgate of a MOSFET device configured to generate output signals based on sensed chemical characteristics. The AC signal has a frequency greater than that of a voltage signal at a gate of the MOSFET and the AC signal modulates the signal generated by the MOSFET.

Figure 1:
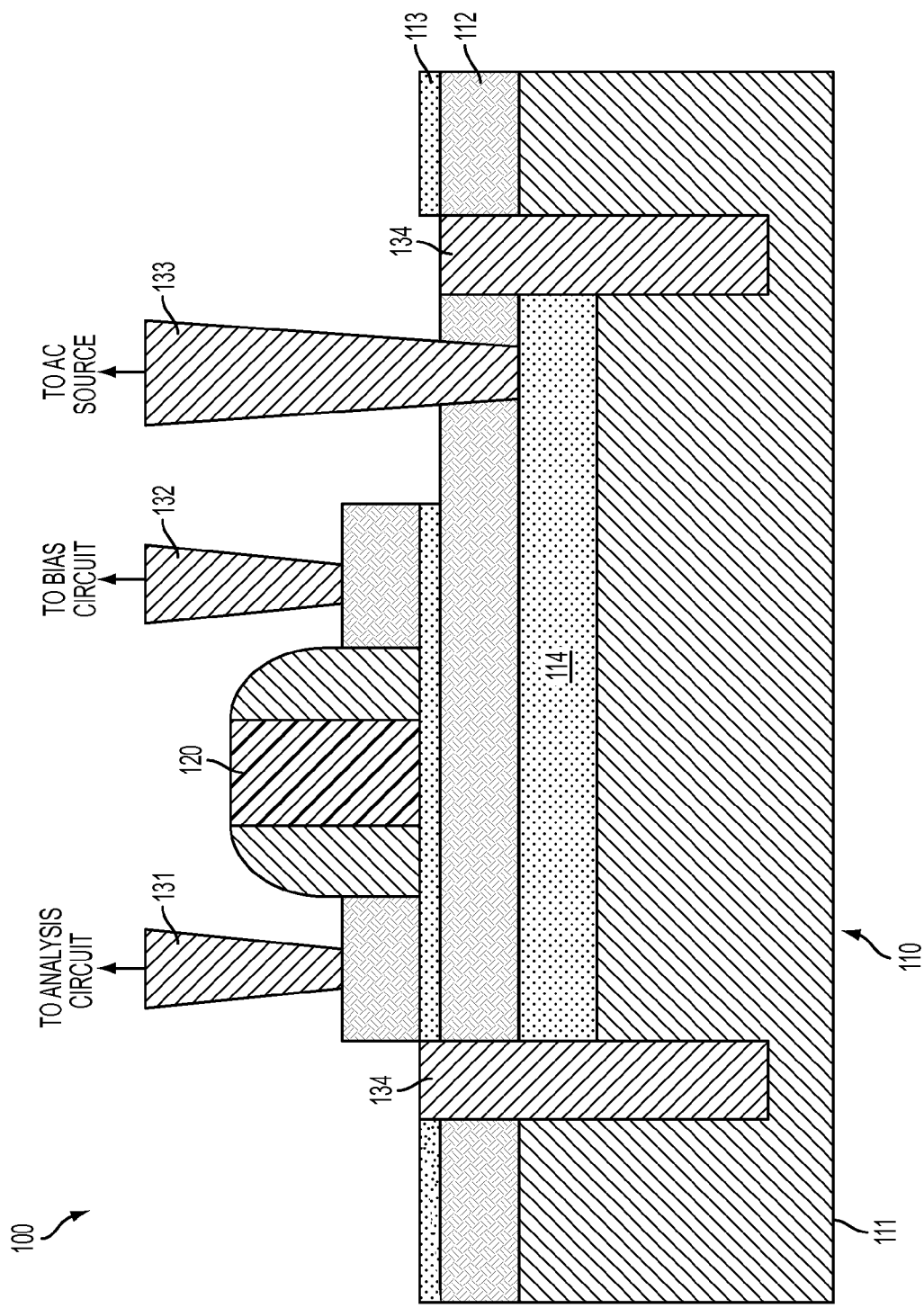
FIG. 1 illustrates a metal-oxide-semiconductor field effect transistor (MOSFET) according to one embodiment.

FIG. 1 illustrates a metal-oxide semiconductor field effect transistor (MOSFET) device 100 according to an embodiment of the disclosure. The MOSFET device 100 includes a substrate body 110 including a substrate layer 111, a buried oxide (BOX) layer 112, and a semiconductor layer 113 formed on the substrate layer 111. The substrate layer 111 may be an undoped semiconductor substrate layer. The BOX layer 112 may be a thin BOX layer, having a thickness of 30 nanometers (nm) or less. The semiconductor layer 112 may be a silicon-on-insulator (SOI) layer. In one embodiment, the semiconductor layer 112 is a fully depleted silicon-on-insulator (FDSOI) layer. The substrate body 110 further includes a backgate 114. The backgate 114 may be buried within the substrate body 110 beneath the FDSOI layer.

A gate 120 is formed on the semiconductor layer 113, and conductive leads 131 and 132 are located on the semiconductor layer 113 to form a source and a drain. A conductive lead 133, or backgate contact 133, is formed to contact the backgate 114. Shallow trench isolators 134 are formed to separate the MOSFET device 100 from adjacent devices.

In one embodiment, the gate 120 may include a chemical substance that generates an electrical signal based on the chemical characteristics of a substance contacting the gate 120. In another embodiment, the gate 120 may be connected to a sensing pad configured to generate electrical signals based on chemical characteristics of a substance in contact with the sensing pad. The drain 131 may be connected to an analysis circuit, and the drain 132 may be connected to a bias circuit. The backgate contact 133 may be connected to an AC voltage source.

In operation, a current from the bias circuit to the analysis circuit 131 is altered according to the voltage potential at the gate 120 based on sensed chemical characteristics. In one embodiment, the bias circuit provides a DC potential at the source 132. In another embodiment the bias circuit may be a resistor or a transistor load. For example, if a high concentration of a chemical is sensed by the gate 120 or a sensing pad connected to the gate 120, a current may flow from the source 132, through the transistor channel, to the drain 131, and to the analysis circuit may be high to correspond to the sensed chemical characteristic. An AC voltage is applied to the backgate contact 133 to alter the threshold voltage of the transistor, which in turn alters the current flow from the current source to the analysis circuit. In this manner, the AC voltage modulates the signal generated by the gate 120 based on the sensed chemical characteristics.

In one embodiment, the sensed chemical characteristics vary at a rate of less than 1 Hz. In other words, the input signals generated by a sensing pad may have a substantially direct current (DC) characteristic having a voltage level that is maintained constant for a long period of time relative to a time in which the voltage level on the backgate changes. In another embodiment, the sensed chemical characteristics vary at a rate of less than about 1 kHz.

In one embodiment of the present disclosure, the AC source generates an AC signal having a frequency of greater than 1 kHz. For example, in one embodiment the AC source generates an AC signal having a frequency of greater than 10 kHz, and in one embodiment, the frequency is around 1 MHz. Accordingly, even when a frequency of a signal generated based on a potential at the gate 120 is low and susceptible to the effects of MOSFET flicker noise, the signal generated based on the potential at the gate 120 may be modulated by an AC signal at the backgate 114 having a frequency that is less susceptible to flicker noise, such as a frequency above 1 kHz.

Figure 2:
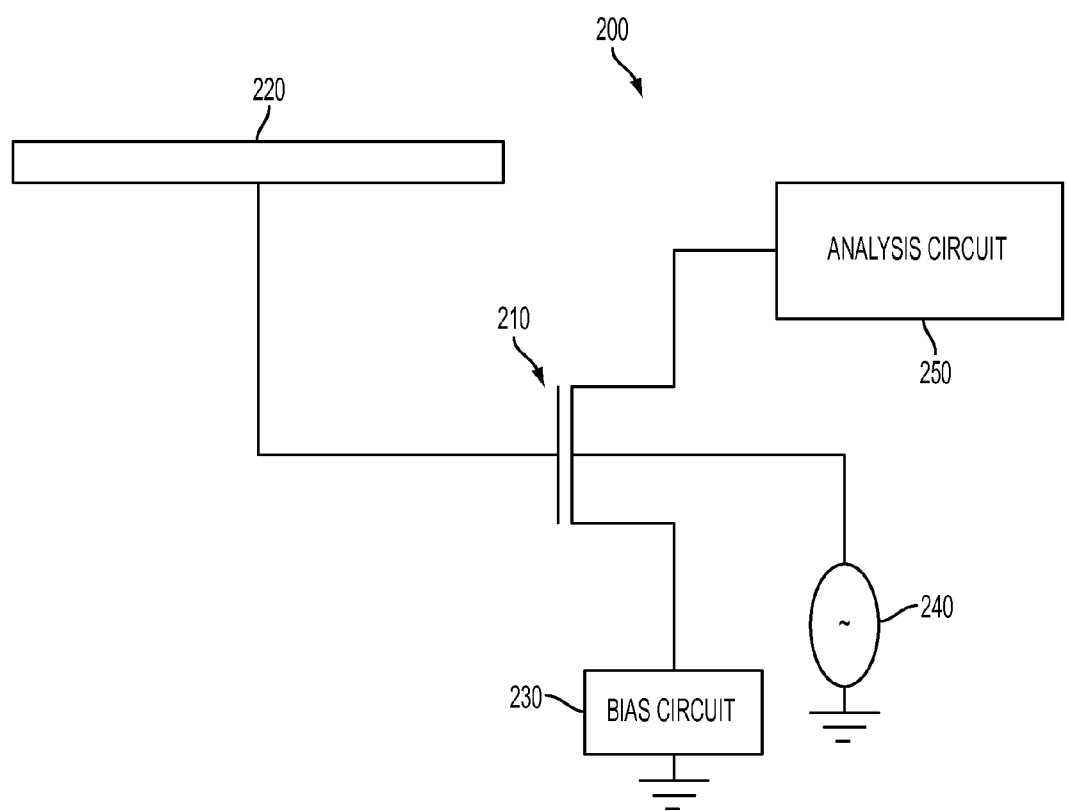
FIG. 2 illustrates a MOSFET assembly according to one embodiment.

FIG. 2 illustrates a circuit diagram of a MOSFET assembly 200 according to an embodiment of the present disclosure. The assembly 200 includes a MOSFET 210, a sensing pad 220 connected to a gate of the MOSFET 210, a bias circuit 230 connected to the source of the MOSFET 210, an analysis circuit 250 connected to the drain of the MOSFET 210, and an AC voltage source 240 connected to a backgate of the MOSFET 210.

In some embodiments, the MOSFET 210 may be an FDSOI MOSFET. The MOSFET 210 may have a thin BOX, having a thickness of 30 nm or less.

The sensing pad 220 may comprise any type of chemically-reactive pad, surface, or device configured to interact with a chemical in a substance and generate a signal based on the interaction. For example, the sensing pad 220 may include at least one reactive layer that reacts with a chemical to generate an electrical voltage. The signal generated by the sensing pad 220 controls a potential at a gate of the MOSFET 210, varying a current that flows between the source and drain of the MOSFET 210. The change of the current is detected by the analysis circuit 250 and analyzed to determine chemical characteristics of the substance based on the signals from the sensing pad 220.

The analysis circuit 250 may include an analog-to-digital (A/D) converter, amplifier, a processor, comparator, memory, and any other logic for analyzing the signals output from the MOSFET 210 based on the signals output from the sensing pad 220.

The AC voltage source 240 may have a frequency greater than 1 kHz. For example, in one embodiment the AC voltage source 240 generates an AC signal having a frequency in a range between about 10 kHz and 10 MHz, such as about 1 MHz.

In operation, the sensing pad 220 is exposed to a substance having a particular chemical characteristic. A chemical of the sensing pad 220 reacts with the substance to generate a signal based on the particular chemical characteristic of the substance. For example, a higher concentration of a chemical may result in a signal having a higher voltage output from the sensing pad 220, and a lower concentration of the chemical may result in a signal having a lower voltage output from the sensing pad 220. The voltage level of the signal output from the sensing pad 220 affects a potential at a gate of the MOSFET 210, altering a current passing through the MOSFET 210.

The source terminal of the MOSFET 210 is connected to a bias circuit such as a current source 230 and the drain terminal is connected to the analysis circuit 250. In one embodiment in which the MOSFET 210 is a negative channel field effect transistor (NFET), when a voltage potential at the gate changes, based on the signal from the sensing pad 220, the analysis circuit 250 senses a change in current flow. Conversely, when the gate is turned off, or when the voltage potential at the gate decreases, the analysis circuit 250 senses a decrease in current flow. Accordingly, the analysis circuit 250 may determine chemical characteristics of a substance based on a level of current that is permitted to flow through the MOSFET 210 based on the signal generated by the sensing pad 220. It is understood that embodiments of the disclosure encompass a positive channel field effect transistor (PFET) transistor in which an activation process of the MOSFET 210 is reversed.

An AC signal is applied to a backgate of the MOSFET 210 at a frequency greater than a frequency at which the signal output from the sensing pad 220 changes. The frequency of the AC signal may be orders of magnitude greater than a frequency of the signal output from the sensing pad 220. In one embodiment, a frequency of the signals output from the sensing pad is less than 1 Hz and a frequency of the AC signal is greater than 1 kHz. In one example, the signal output from the sensing pad is substantially a DC signal, and the AC signal has a frequency in a range between 10 kHz and 10 MHz, such as 1 MHz. The AC signal changes voltage potential that is required at the gate of the MOSFET 210 to allow current to flow through the MOSFET 210. As a result, the AC signal modulates the signal output from the sensing pad 220. Accordingly, even when a frequency of the signal output from the sensing pad is low and subject to MOSFET flicker noise, the frequency of the current flowing through the MOSFET may be increased to reduce the susceptibility of the signals generated by the MOSFET to the MOSFET flicker noise.

Figure 3:
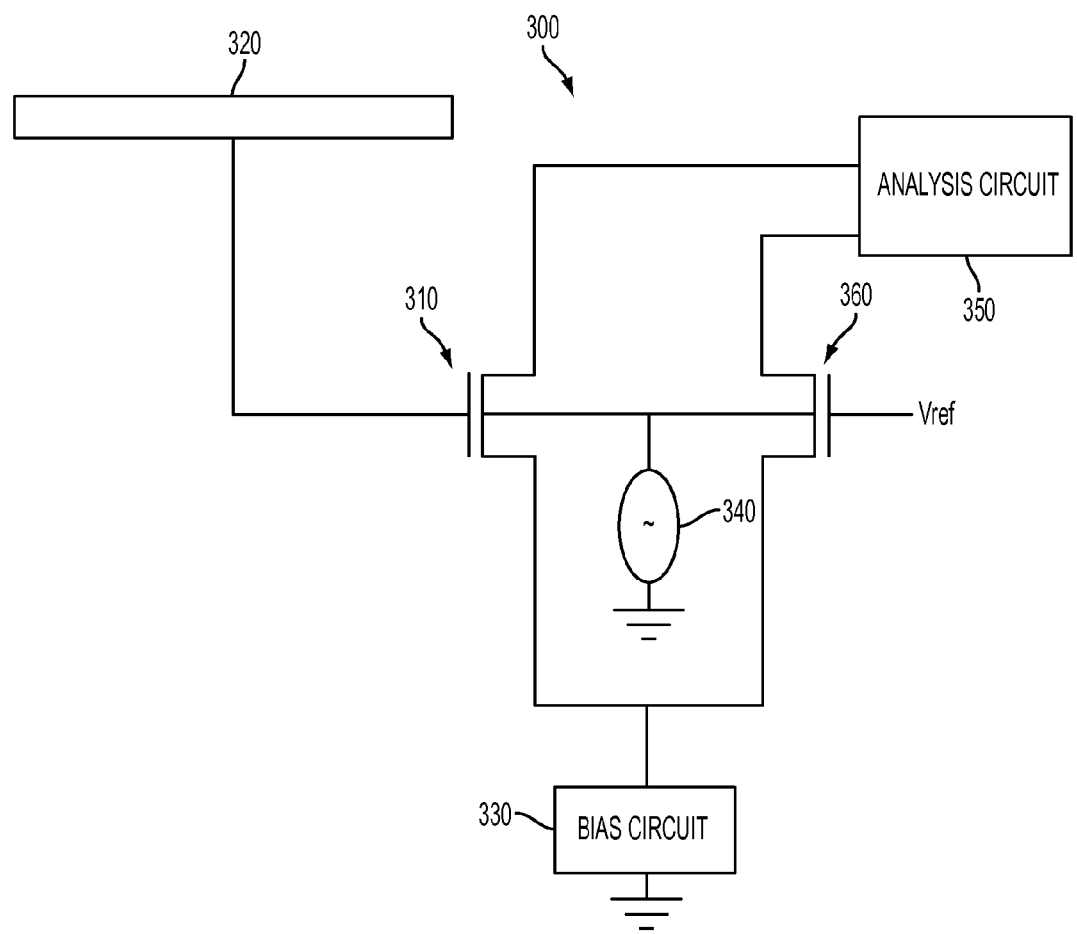
FIG. 3 illustrates a differential MOSFET assembly according to an embodiment.

FIG. 3 illustrates a differential MOSFET assembly 300 according to an embodiment of the present disclosure. The assembly 300 includes a first MOSFET 310, or a sensing MOSFET 310, a sensing pad 320 connected to a gate of the sensing MOSFET 310, a bias circuit 330 connected to the source of the sensing MOSFET 310, an analysis circuit 350 connected to drain of the sensing MOSFET 310, and an AC voltage source 340 connected to a backgate of the sensing MOSFET 310. In one embodiment the bias circuit is a DC current source. The sensing pad 320, current source 330, analysis circuit 350, and AC voltage source 340 may correspond to the sensing pad 220, current source 230, analysis circuit 250, and AC voltage source 240 of FIG. 2.

The differential MOSFET assembly 300 further includes a second MOSFET 360, or reference MOSFET 360, having a reference voltage provided to a gate, a backgate connected to the AC voltage source 340, a source connected to the current source 330, and a drain connected to the analysis circuit 350. The reference voltage may maintain a gate of the reference MOSFET at a predetermined potential so that a signal output from the reference MOSFET 360 to the analysis circuit 350 is changed only based on the modulation provided by the AC voltage source 340. In other words, the reference voltage may be a constant DC voltage in contrast to the sensing voltage at the gate of the sensing MOSFET 310 which changes based on a sensed chemical characteristic. The analysis circuit 350 may determine the chemical characteristics of a substance contacting the sensing pad 320 based on a comparison of the modulated signal output from the sensing MOSFET 310 and the modulated reference signal output from the reference MOSFET 360.

In one embodiment, the potential at the gate of the reference MOSFET 360 can be determined by a circuit that adjusts this potential to cancel out drift or aging of the sensing MOSFET 310. In this case the potential at the gate of reference MOSFET 360 is determined such that the difference in the current flow at the drain terminal of the reference MOSFET 360 and sensing MOSFET 310 is equal to zero when the chemical substance to be sensed in not exposed to the sensing pad 320.

Figure 4:
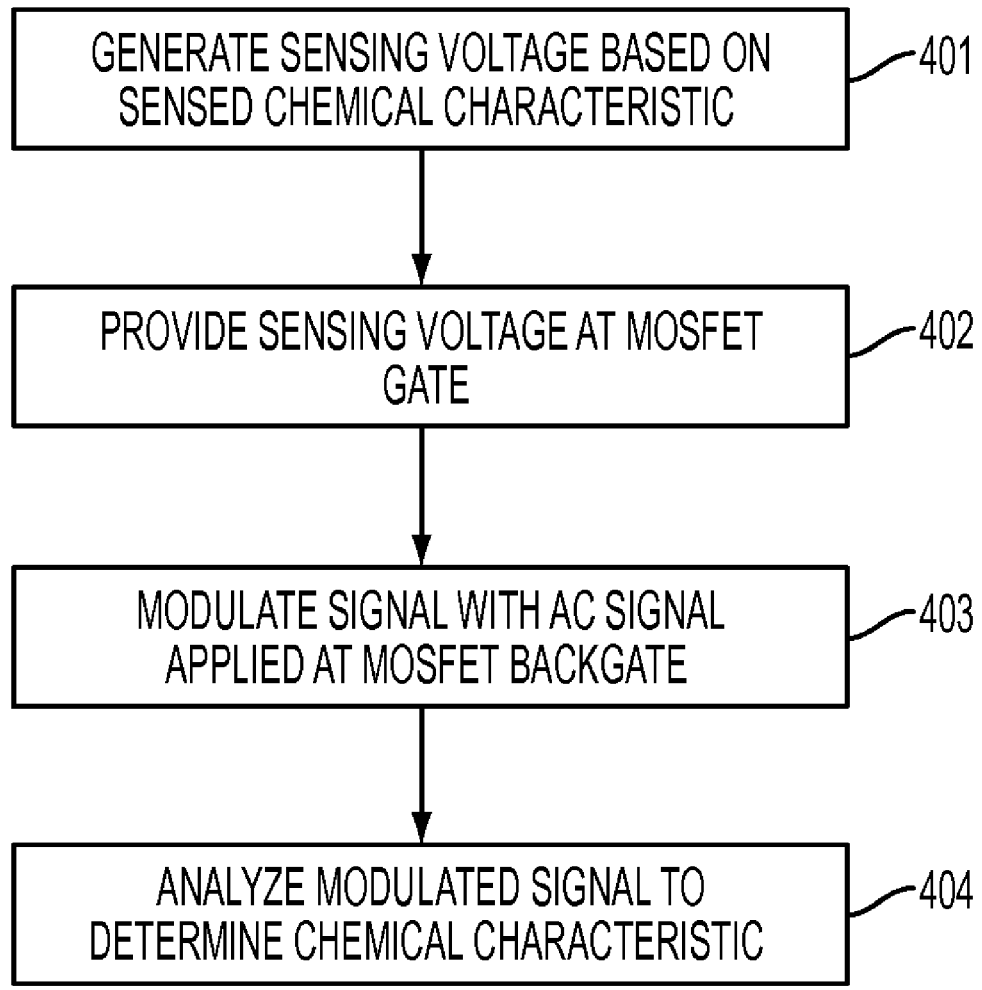
FIG. 4 illustrates a flow diagram of a method according to an embodiment.

FIG. 4 illustrates a flow diagram of a method according to an embodiment of the present disclosure. In block 401, a sensing voltage is generated based on a chemical characteristic of a substance and provided to a gate of a MOSFET in block 402. For example, a gate of a MOSFET may have a sensing layer, and may generate a voltage that varies according to varying chemical characteristics of a substance that comes into contact with the sensing layer. Chemical characteristics may include, for example, types of chemicals, concentrations of chemicals, densities, or any other characteristic. Alternatively, a gate of a MOSFET may be in conductive contact with a sensing mechanism, such as a sensing pad, that generates a signal based on a sensed chemical characteristic. Although a sensing voltage is described, it is understood that any electrical characteristic may be generated capable of altering a potential at a gate of a sensing MOSFET.

In block 403, an AC signal is provided at a backgate of the MOSFET to modulate a signal output from the MOSFET based on the generated sensing voltage. The AC signal may have a frequency greater than 1 kHz, such as in a range from about 10 kHz to about 10 MHz. The MOSFET may be an FDSOI MOSFET and may have a thin buried oxide layer (BOX), having a thickness of 30 nm or less.

In block 404, a chemical characteristic is determined by analyzing the modulated signal output from the MOSFET based on the sensing voltage. For example, the modulated signal may be converted from an analog signal to a digital signal, amplified, de-modulated, and processed to compare the signal with predetermined voltages indicating different chemical characteristics.

As a result, even when a frequency of the sensing voltage signal is low and subject to MOSFET flicker noise, the frequency of the current flowing through the MOSFET may be increased to reduce the susceptibility of the signals generated by the MOSFET to the MOSFET flicker noise, and chemical characteristics may be accurately analyzed.

Figure 5:
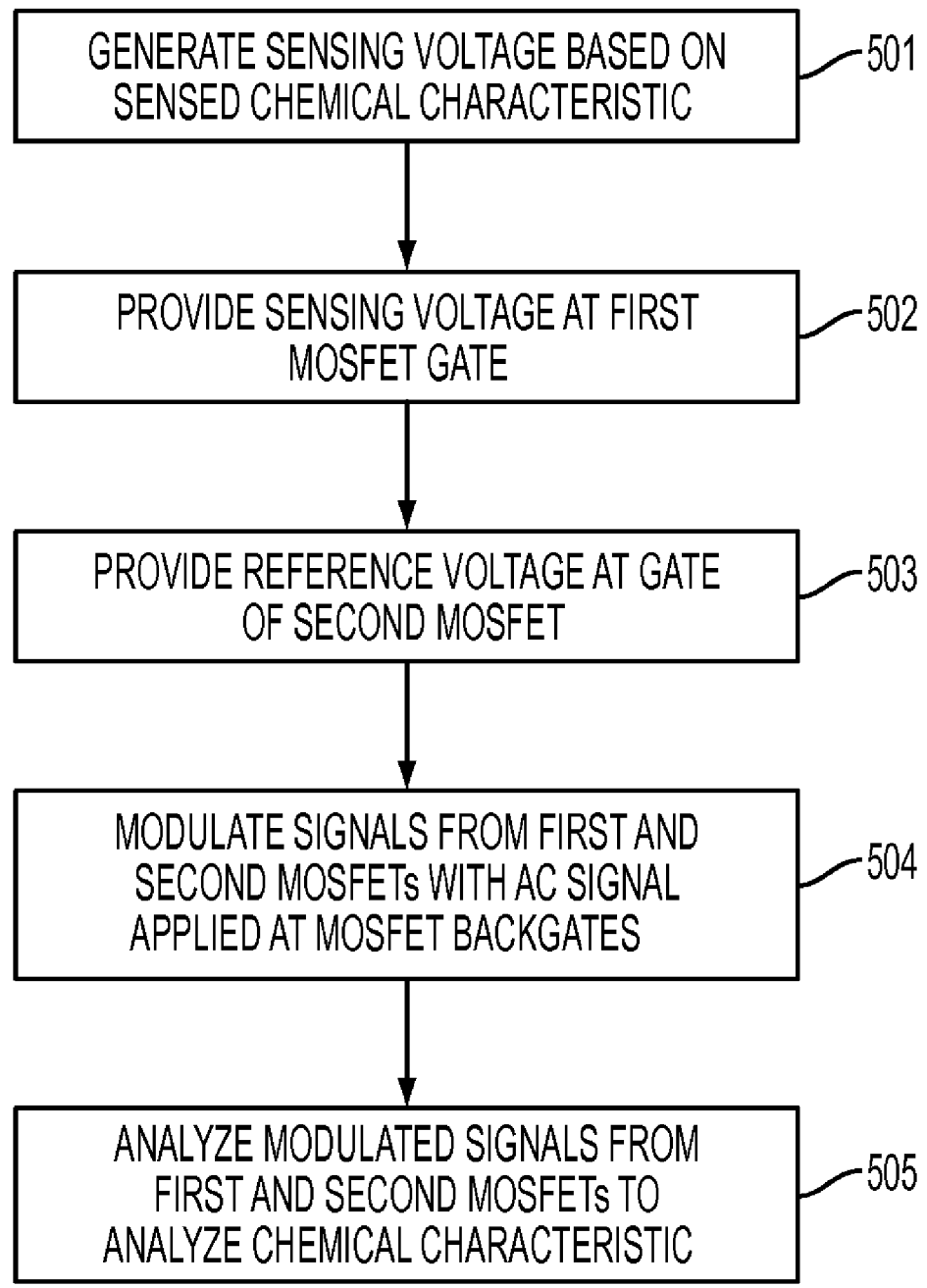
FIG. 5 illustrates a flow diagram of a method according to another embodiment.

FIG. 5 illustrates a flow diagram of a method according to another embodiment of the present disclosure. In block 501, a sensing voltage is generated based on a chemical characteristic of a substance and provided to a gate of a first MOSFET, or a sensing MOSFET, in block 502. For example, the gate of the first MOSFET may have a sensing layer, and may generate a voltage that varies according to varying chemical characteristics of a substance that comes into contact with the sensing layer. Chemical characteristics may include, for example, types of chemicals, concentrations of chemicals, densities, or any other characteristic. Alternatively, the gate of the first MOSFET may be in conductive contact with a sensing mechanism, such as a sensing pad, that generates a signal based on a sensed chemical characteristic. Although a sensing voltage is described, it is understood that any electrical characteristic may be generated capable of altering a potential at the gate of the first MOSFET.

In block 503, a reference voltage is provided at a gate of a second MOSFET, or a reference MOSFET. Each of the first and second MOSFET may be connected between a same current source and an analysis circuit.

In block 504, an AC signal is provided at a backgate of the first and second MOSFETs to modulate signals output from the MOSFETs. In particular, the AC signal modulates the signal from the first MOSFET based on the generated sensing voltage and modulates the signal from the second MOSFET based on the reference voltage. The AC signal may have a frequency greater than 1 kHz, such as in a range between about 10 kHz and about 10 MHz.

In block 505, a chemical characteristic is determined by analyzing the modulated signal output from the first MOSFET based on the sensing voltage and the modulated signal output from the second MOSFET based on the reference voltage. For example, the modulated signals may be converted from an analog signal to a digital signal, amplified, de-modulated, and processed to compare the signals with each other, and to compare the difference between the signals with predetermined voltage levels indicating different chemical characteristics.

As a result, even when a frequency of the sensing voltage signal is low and subject to MOSFET flicker noise, the frequency of the current flowing through the first MOSFET may be increased to reduce the susceptibility of the signals generated by the first MOSFET to the MOSFET flicker noise, and chemical characteristics may be accurately analyzed.

Figure 6:
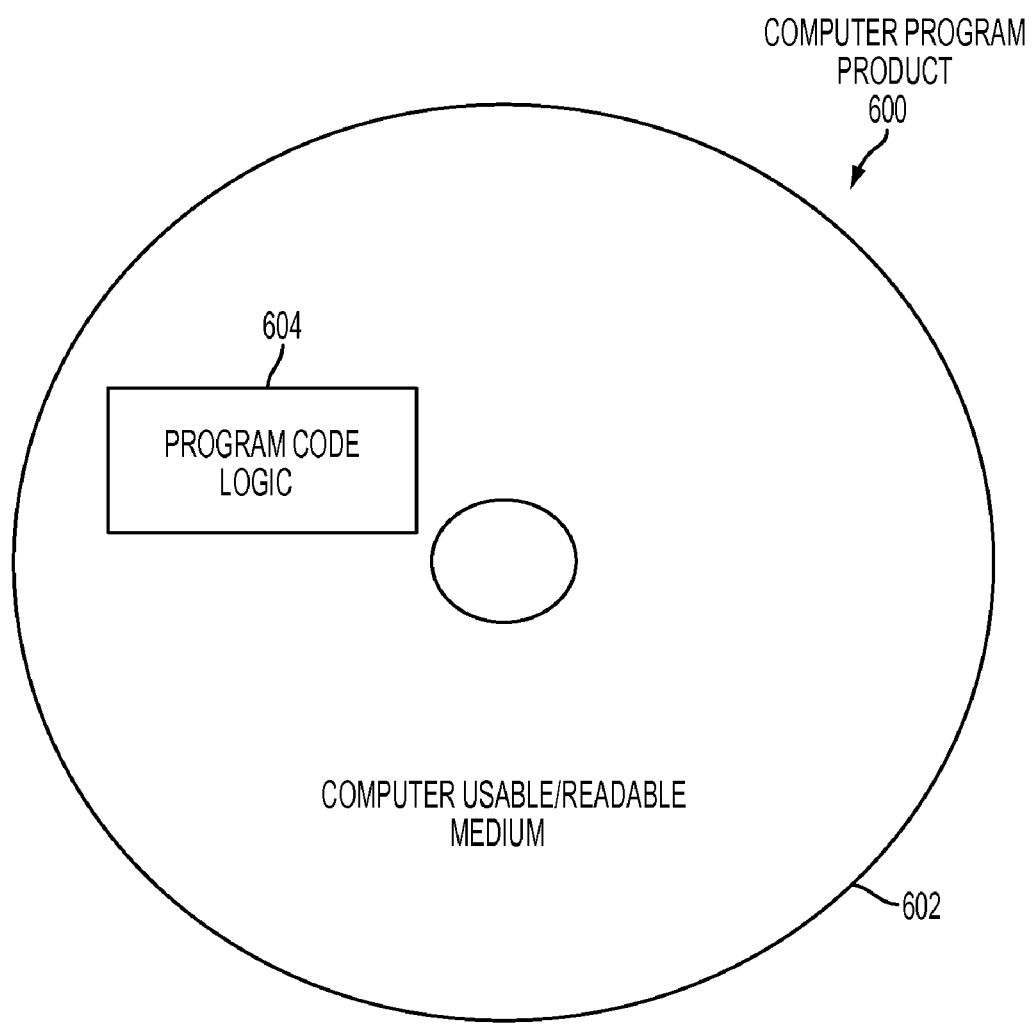
FIG. 6 illustrates a computer-readable storage medium according to an embodiment.

As described above, embodiments can be embodied in the form of computer-implemented processes and apparatuses for practicing those processes. An embodiment may include a computer program product 600 as depicted in FIG. 6 on a computer readable/usable medium 602 with computer program code logic 604 containing instructions embodied in tangible media as an article of manufacture. Exemplary articles of manufacture for computer readable/usable medium 602 may include floppy diskettes, CD-ROMs, hard drives, universal serial bus (USB) flash drives, or any other computer-readable storage medium, wherein, when the computer program code logic 604 is loaded into and executed by a computer, the computer becomes an apparatus for practicing the invention. Embodiments include computer program code logic 604, for example, whether stored in a storage medium, loaded into and/or executed by a computer, or transmitted over some transmission medium, such as over electrical wiring or cabling, through fiber optics, or via electromagnetic radiation, wherein, when the computer program code logic 604 is loaded into and executed by a computer, the computer becomes an apparatus for practicing the invention. When implemented on a general-purpose microprocessor, the computer program code logic 604 segments configure the microprocessor to create specific logic circuits.

According to embodiments of the present disclosure, an AC signal is provided to a backgate of a MOSFET device configured to generate output signals based on sensed chemical characteristics. The AC signal has a frequency greater than that of a voltage signal at a gate of the MOSFET and the AC signal modulates the signal generated by the MOSFET. The voltage signal at the gate of the MOSFET corresponding to a sensed chemical characteristic may have a frequency of less than 1 Hz, and may be a substantially DC voltage signal. The AC signal may modulate the gate voltage signal to a frequency greater than 1 kHz, resulting in signals generated by the MOSFET that are less susceptible to MOSFET flicker noise.

Embodiments of the present disclosure further encompass a differential circuit including a second MOSFET having a reference voltage applied to its gate, and the chemical characteristics sensed by the first MOSFET may be analyzed by comparing the output signals of the first MOSFET and the second MOSFET.

Aspects of the present invention are described above with reference to flowchart illustrations and/or block diagrams of methods, apparatuses or systems according to embodiments of the disclosure. It will be understood that some blocks of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, blocks in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

What is claimed is:

1. A method, comprising:
   receiving a voltage potential at a gate of a first MOSFET based on a sensed chemical characteristic;
   receiving at a backgate of the first MOSFET an AC voltage signal; and
   analyzing, with an analysis circuit connected to one of a first source and a first drain of the MOSFET, the sensed characteristic based on the receiving the voltage potential at the gate of the first MOSFET.

2. The method of claim 1, wherein receiving the voltage potential at the gate of the first MOSFET includes generating a sensing voltage based on a chemical reaction of a sensed substance with a sensing surface.

3. The method of claim 1, further comprising:
   receiving at the other of the first source and the first drain of the first MOSFET a current from a bias circuit.

4. The method of claim 1, further comprising:
   receiving at a gate of a second MOSFET a reference voltage; and
   receiving at a backgate of the second MOSFET the AC voltage signal,
   wherein one of a second source and a second drain of the second MOSFET is connected to the analysis circuit.

5. The method of claim 4, further comprising:
   receiving at the other of the first source and the first drain of the first MOSFET a current from a bias circuit; and
   receiving at the other of the second source and the second drain of the second MOSFET a current from the bias circuit.

6. The method of claim 4, wherein analyzing the sensed characteristic includes comparing a modulated sensing signal output from the first MOSFET with a modulated reference signal output from the second MOSFET.

7. The method of claim 1, wherein analyzing the sensed characteristic includes converting a signal based on the receiving the voltage potential at the gate of the first MOSFET from an analog to a digital signal and amplifying the signal.

8. The method of claim 1, wherein a sensing signal corresponding to the received voltage potential is a substantially direct current (DC) signal.

9. The method of claim 1, wherein the AC voltage signal has a frequency greater than 1 kHz.

10. A method comprising:
    generating a sensing voltage based on a sensed chemical characteristic;
    providing the sensing voltage to a gate of a first MOSFET; and
    modulating the sensing voltage with an AC voltage signal applied to a backgate of the first MOSFET to generate a modulated sensing signal.

11. The method of claim 10, further comprising:
    analyzing the modulated sensing signal to analyze the sensed chemical characteristic.

12. The method of claim 11, wherein analyzing the modulated sensing signal includes at least one of de-modulating the modulated sensing signal, converting the modulated sensing signal from an analog signal to a digital signal, amplifying the modulated sensing signal, and comparing the modulated sensing signal to predetermined voltages corresponding to predetermined chemical characteristics.

13. The method of claim 10, wherein the sensing voltage corresponds to a sensing signal having a frequency less than 1 Hz.

14. The method of claim 13, wherein the sensing signal is substantially a direct current (DC) signal.

15. The method of claim 10, wherein the AC voltage signal has a frequency greater than 1 kHz.

16. The method of claim 15, wherein the AC voltage signal has a frequency greater than around 10 kHz.

17. The method of claim 10, wherein the sensing signal is substantially a direct current (DC) signal and the AC voltage signal has a frequency greater than 1 kHz.

18. The method of claim 10, further comprising:
   providing a reference voltage to a gate of a second MOSFET;
   modulating the reference voltage with the AC voltage signal applied to a backgate of the second MOSFET to generate a modulated reference signal; and
   analyzing the sensed chemical characteristic by comparing the modulated reference signal output from the second MOSFET with the modulated sensing signal output from the first MOSFET.

19. The method of claim 18, further comprising:
   providing a current from a bias circuit to one of a source and a drain of each of the first and second MOSFETs.

20. The method of claim 10, wherein the first MOSFET is a fully depleted silicon-on-insulator (FDSOI) MOSFET having a buried oxide (BOX) layer with a thickness less than 30 nanometers.

* * * * *